United States Patent [19]

Bryce et al.

[11] Patent Number: 5,770,626
[45] Date of Patent: Jun. 23, 1998

[54] TETRAHYDRONAPHTALENE AND INDANE COMPOUNDS USEFUL FOR REVERSING THE PHOTODAMAGE IN SUN-EXPOSED SKIN

[75] Inventors: Graeme Findlay Bryce, Upper Montclair; Stanley Seymour Shapiro, Livingston, both of N.J.

[73] Assignee: Hoffmann-La Roche Inc., Nutley, N.J.

[21] Appl. No.: 520,166

[22] Filed: May 8, 1990

Related U.S. Application Data

[63] Continuation of Ser. No. 219,616, Jul. 14, 1988, abandoned, which is a continuation-in-part of Ser. No. 86,992, Aug. 19, 1987, abandoned.

[51] Int. Cl.$^6$ ................................................. A61K 31/10
[52] U.S. Cl. ........................ 514/709; 514/710; 514/725
[58] Field of Search ................................... 514/710, 725, 514/709

[56] References Cited

U.S. PATENT DOCUMENTS

| | | | |
|---|---|---|---|
| 4,396,553 | 8/1983 | Klaus | 2560/456 MS |
| 4,877,805 | 10/1989 | Kligman . | |
| 4,888,342 | 12/1989 | Kligman | 514/419 |

FOREIGN PATENT DOCUMENTS

| | | |
|---|---|---|
| 0253393 | 1/1988 | European Pat. Off. . |
| 906000 | 9/1962 | United Kingdom . |

Primary Examiner—Marianne M. Cintins
Attorney, Agent, or Firm—George W. Johnston; William H. Epstein

[57] ABSTRACT

The use of compounds of formula I as topical agents to combat the disorders of the skin produced by photodamage which disorders include: wrinkling, elastosis and premature aging is described. Compounds of formula I are

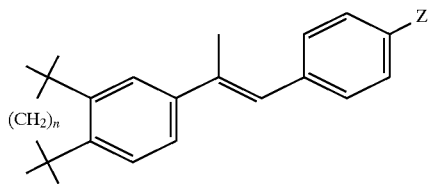

wherein n represents 1 or 2, Z represents —SO$_2$R, wherein R represents lower-alkyl, lower-alkenyl, lower-alkynyl, lower-alkoxy-lower-alkyl, lower-alkanoyl-lower-alkyl, hydroxy-lower-alkyl, halo-lower-alkyl, lower-carbalkoxy-lower-alkyl, lower-alkoxy, hydroxy, mono-lower-alkyl amino or di-lower-alkylamino and pharmaceutically acceptable salts thereof.

14 Claims, No Drawings

TETRAHYDRONAPHTALENE AND INDANE COMPOUNDS USEFUL FOR REVERSING THE PHOTODAMAGE IN SUN-EXPOSED SKIN

RELATED APPLICATIONS

This application is a continuation of application Ser. No. 07/219,616, filed Jul. 14, 1988, now abandoned, which is a continuation-in-part of Ser. No. 086,992 filed Aug. 19, 1987, now abandoned.

BACKGROUND OF THE INVENTION

The skin, particularly in humans, contains an elaborate network of elastin fibers which are responsible for maintaining its elastic properties. With excessive exposure to sunlight the elastic fiber system becomes hyperplastic, disorganized and ultimately disrupted. This is known as actinic elastosis and is the principal cause of wrinkling, discoloration and laxity of the skin in the exposed areas of the body. The skin can repair itself to some extent but it is nevertheless desirable to have an agent which can accelerate the repair of this prematurely aged skin.

The UVB irradiated hairless mouse has been found to be a convenient model for actinic elastosis in the skin. (Kligman et al. J. Invest. Dermatol. 78:181 (1982). It has been shown by Johnston et al. in J. Invest. Dermatol. 82:587 (1984) that irradiation with low levels of UVB which simulate realistic solar exposure leads to a significant increase in skin elastin as measured by desmosine content. The amount of this amino acid, which is isolated from acid hydrolysis of elastin, is proportional to the elastin present in the skin. (Uitto et al., Lab. Invest. 49:1216 (1973). Treatment of irradiated mice with topical retinoic acid has been shown to normalize the histological features of the skin in which the previously elastotic dermis has the appearance of unirradiated tissue (Kligman et al., Conn. Tissue Res. 12:139 (1984), Kligman U.S. Pat. No. 4,603,146 Jul. 1986). Therefore this model can be used to determine the efficacy of compounds in the repair of sum damaged skin.

SUMMARY OF THE INVENTION

In accordance with this invention, compounds of formula

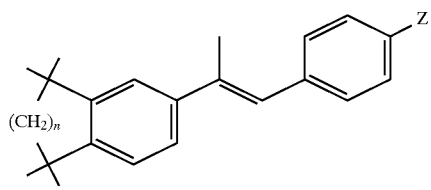

wherein n represents 1 or 2; Z represents —SO$_2$R, wherein R represents lower-alkyl, lower-alkenyl, lower alkynyl, lower-alkoxy-lower-alkyl, lower-alkanoyl-lower-alkyl, hydroxy-lower-alkyl, halo-lower-alkyl, lower-carbalkoxy-lower-alkyl, lower-alkoxy, hydroxy, mono-lower-alkyl amino or di-lower-alkylamino,
and pharmaceutically acceptable salts thereof applied topically to the skin of a patient reverses the conditions associated with photodamage. Hence, by the topical application of compounds of formula I to the skin of patients which has been damaged through sun exposure, the effects of wrinkling, elastosis and premature aging can be reversed leading to an improvement in the appearance of the skin.

Through the topical administration of the compounds of the formula I, the acceleration of repair of dermal damage is accomplished so as to provide the skin with a smoother and younger appearance.

DETAILED DESCRIPTION

The term "lower" as used herein denotes groups which preferably contain 1–4 carbon atoms. Alkyl groups can be straight-chain or branched-chain. Preferred lower-alkyl groups are methyl, ethyl and isopropyl. Examples of lower-alkenyl groups are vinyl, allyl and methallyl. Examples of lower-alkanoyl groups are acetyl, propionyl, and butyryl. Alkynyl groups can be straight-chain or branched-chain. Preferred lower alkynyl groups are ethynyl and propynyl. The term "halogen" embraces fluorine, chlorine, bromine and iodine, of which chlorine is preferred. Examples of lower-carbalkoxy-lower-alkyl groups are carbomethoxy- and carboethoxy-methyl and -ethyl. Examples of lower-alkoxy groups are methoxy and ethoxy. Examples of alkylamino groups are methylamino, ethylamino, isopropylamino, dimethylamino and diethylamino.

The invention relates to tetrahydronaphthalene and indane compounds of the formula

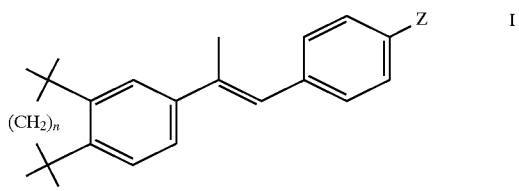

wherein n represents 1 or 2; Z represents a group —SO$_2$R, wherein R represents lower-alkyl, lower-alkenyl, lower alkynyl, lower-alkoxy-lower-alkyl, lower-alkanoyl-lower-alkyl, hydroxy-lower-alkyl, halo-lower-alkyl, lower-carbalkoxy-lower-alkyl, lower-alkoxy, hydroxy, mono-lower-alkylamino or di-lower-alkyl-amino
and pharmaceutically acceptable salts thereof.

A pharmaceutically acceptable salt of compounds of formula I, which compounds belong to the class of retinoids, includes any salt chemically permissible in the art for compounds of formula I and applicable to human patients in a pharmaceutically acceptable preparation. Among such pharmaceutically acceptable salts of compounds of formula I there are especially included salts of sulfonic acids of compounds of formula I. Any conventional pharmaceutically acceptable base salt of sulfonic acids of formula I can be utilized. Among the conventional base salts which can be utilized there are included, for example, alkali metal salts such as sodium or potassium, alkaline earth metal salts such as calcium or magnesium, and ammonium or alkyl ammonium salts. Furthermore, conventional acid addition salts, such as acetates, may be utilized for compounds of formula I wherein R is mono- lower-alkylamino or di-lower-alkylamino.

Of the compounds of formula I wherein Z represents —SO$_2$R, there are preferred those compounds in which R is lower-alkyl, lower-alkenyl, hydroxy-lower-alkyl, lower-alkoxy, hydroxy, mono-lower-alkylamino or di-lower-alkylamino.

Furthermore, there are especially preferred compounds of formula I in which R is lower-alkyl. Further preferred compounds of formula I are those in which n of formula I is 2.

The following compounds of formula I are especially preferred:
methyl p-[2-(5,6,7,8-tetrahydro-5,5,8,8-tetramethyl-2-naphthyl)propenyl]phenylsulfone; and ethyl p-[2-(5,6,7,8-tetrahydro-5,5,8,8-tetramethyl-2-naphthyl)propenyl]phenylsulfone.

Another interesting compound of Formula is:

isopropyl p-[2-(5,6,7,8-tetrahydro-5,5,8,8-tetramethyl-2-naphthyl)propenyl]phenylsulfone.

Processes for preparing compounds of Formula I are set forth in U.S. Pat. No. 4,396,553 which is hereby incorporated by reference.

The compounds of the formula I when applied topically to the skin, reverse the conditions associated with photodamage so as to moderate and retard the damage to the skin caused by sun exposure. The damage caused by sun exposure may include premature aging, elastosis and wrinkling. This damage is more pronounced in older patients. By applying the compounds of formula I topically to the skin in an amount effective to reverse the conditions associated with photodamage, the acceleration of skin repair is accomplished to enhance the skin with a smoother and younger appearance. The compounds of formula I should be applied to that portion or area of the skin which is affected by photodamage or in which treatment is desired. The use of the compounds of formula I in accordance with this invention can provide the effects of anti-aging and anti-wrinkling, as well as enhance the repair of sun damaged skin.

A compound of formula I, or a combination of compounds of formula I can be applied in accordance with this invention to human skin in conventional topical compositions. These compositions can be utilized to apply compounds of formula I to the skin of the body, particularly the face, legs, arms and hands. The preferred method of application of compounds of formula I topically to produce the best effects should start where a patient is between 30 and 55 years of age, when elastosis begins to appear and becomes more pronounced. Thereafter, this composition can be continuously applied to patients to reduce the effects and injury associated with sun exposure. Generally, it is preferred to begin the treatment when the patient reaches approximately 30 years of age and to continue the treatment throughout his life, in order that the effects of elastosis be reduced and to prevent any further progression of photodamage.

The compounds of formula I can be administered in accordance with this invention in any conventional suitable topical preparation, i.e. in combination with any suitable conventional carrier useful for topical administration. Therefore, compounds of formula I can be administered in accordance with this invention in any suitable topical composition such as a cream, ointment, soap, solution, lotion, emulsion, shampoo, etc. Generally, for most efficacious results, these topical compositions contain from about 0.00001% to about 1.0% by weight of the total composition of a compound of formula I, with amounts of from about 0.0001% to about 0.1% by weight of the composition being especially preferred. If desired, higher concentrations may be utilized depending upon the nature and extent of elastosis.

In formulating these compositions, any conventional non-toxic, dermatologically acceptable base or carrier in which a compound of formula I is stable can be utilized. The preferred compositions for use in this invention are the conventionally cosmetic compositions which can contain a cosmetically active ingredient which is topically administered to human skin to provide a cosmetic effect. Among the conventional cosmetically active materials which can be utilized in this composition are included: sunscreens, penetration enhancers, moisturizers, surfactants, emollients, colorants, conditioners, bacteriocides, astringents, detergents, etc.

The topical compositions of this invention can, if desired contain suitable sunscreen agents. Any conventional sunscreen agent can be utilized in formulating the formulations containing compounds of formula I which can be utilized in accordance with this invention.

These topical compositions which contain compounds of formula I can contain any of the conventional excipients and additives commonly used in preparing topical compositions. Among the conventional additives or excipients, which can be utilized in preparing these cosmetic compositions in accordance with this invention are preservatives, thickeners, perfumes and the like. In addition, the conventional antioxidants, such as butylated hydroxyanisoles (BHA), ascorbyl palmitate, propyl gallate, citric acid butylated hydroxy toluene (BHT), ethoxyquin, tocopherol, and the like can be incorporated into these compositions. These topical compositions can contain conventional acceptable carriers for topical applications which are generally utilized in these compositions. These compositions may contain thickening agents, humectants, emulsifying agents and viscosity stabilizers, such as those generally utilized. In addition, these compositions can contain flavoring agents, colorants, and perfume which are conventional in preparing cosmetic compositions.

The topical compositions containing compounds of formula I can be applied to the skin and should be preferably applied to the skin at least once a day for at least 2 or 3 times a week. For obtaining the reversal of the elastosis so as to impart to the skin a smooth and younger appearance the topical compositions should be preferably applied for a period of at least five months. After that compositions which contain compounds of formula I should be applied continually to maintain the effect of younger and smoother skin. These preparations can be applied according to the need of the patient as determined by the prescribing physician. In any event, the particular regimen for application of this composition to a patient will typically depend on the age, weight and skin condition of the individual.

The invention is further illustrated in the following examples. These examples are for illustration and are not limitative of the claimed invention.

EXAMPLE 1

Repair of UVB-Induced Dermal Damage in the Hairless Mouse by Compounds of Formula I Hairless mice (HRS/J strain, Jackson Labs, 5–7 weeks old at the start of the experiments) were irradiated three times per week with a bank of 8 Westinghouse Sunlamps (FS40) placed about 20 cm above the animals. The radiation dose was controlled by an International Light Model IL844A Phototherapy Exposure Control and a detector. The UVB dosing schedule was such that individual doses, seldom exceeding $0.06 J/cm^2$, caused minimal erythema but no burning or scarring. There was significant elastosis, detected by histology, after a total dose of about $3.5 J/cm^2$; this was confirmed in measurements of elastin in whole skin by means of a radioimmunoassay for desmosine. Demosine is found in elastin hydrolysates and is derived from crosslinks in the elastin molecule; it is a reliable index of total elastin. Typically, desmosine increased by about 2–3 fold after $3.5 J/cm^2$ of UVB irradiation. To effect repair of the dermal damage, the UVB irradiation was discontinued and animals were treated three times per week with various concentrations of the compounds of formula I dissolved in acetone. Solutions were made up freshly every week at concentrations such that the dose was delivered in 100 $\mu l$ acetone and applied topically to an area of about 10 $cm^2$ on the back of the animal with a plastic pipette; a control group treated with acetone alone was also included.

After 10 weeks of treatment the animals were sacrificed, skin samples were taken and processed by standard methods. A six micron section from each animal was stained for elastin with Luna's stain and the degree of repair measured quantitatively. In this model, repair is defined by the appearance of a normalized dermis extending from the epidermis down to the layer of compressed elastin. The extent of repair was reflected by the width of this zone. In these studies, the area of the zone on a standard length of histological section was measured by an image analyzer and the results are given as total area in mm² per twenty microscopic fields. Data was analyzed by Student's t-test. The results are given in Table I. In Table I, and Table II each group dosed at a particular concentration of compound of formula I contained six to ten animals.

TABLE I

| Group | Repair Zone, mm² |
| --- | --- |
| Control | 0.005 +/- 0.001 |
| 0.2 μg of Compound A | 0.013 +/- 0.002* |
| 0.6 μg of Compound A | 0.019 +/- 0.005* |
| 2 μg of Compound A | 0.029 +/- 0.008* |
| 6 μg of Compound A | 0.007 +/- 0.002 |
| 20 μg of Compound A | 0.010 +/- 0.003 |
| Control | 0.003 +/- 0.001 |
| 0.1 μg of Compound B | 0.011 +/- 0.003 |
| 0.3 μg of Compound B | 0.014 +/- 0.003* |
| 1 μg of Compound B | 0.021 +/- 0.005* |
| 3 μg of Compound B | 0.022 +/- 0.004* |
| 10 μg of Compound B | 0.011 +/- 0.005 |

*P < 0.05,
**P < 0.01,
***P <0.001 vs Control

Throughout the specification,

Compound A is methyl p-[2-(5,6,7,8-tetrahydro-5,5,8,8-tetramethyl-2-naphthyl)-propenyl]phenylsulfone;

Compound B is ethyl p-[2-(5,6,7,8-tetrahydro-5,5,8,8-tetramethyl-2-naphthyl)-propenyl]phenylsulfone;

EXAMPLE 2

Effect of Compounds of Formula I on the Wrinkles Produced in Hairless Mice by UVB-Irradiation Doses of UVB-irradiation sufficient to induce dermal damage in hairless mice were found to cause the appearance of wrinkles on the exposed skin. One skin replica for each animal was taken of these areas using a liquid dental impression material (SILFLO - Flexico Developments Ltd., England). Wrinkles appeared in these impressions as ridges which cast a shadow when illuminated with low angle light. A characteristic of the wrinkling pattern was the occurrence of the ridges in a regularly-spaced array about 2-mm apart. The extent of wrinkling was visually assessed using this line pattern and assigned a value (Wrinkle Index) of zero to 4 with zero representing complete effacement of wrinkling and 4 representing the maximum degree of wrinkling. It was observed that compounds of formula I caused a dose-dependent effacement of the wrinkles with $ED_{50}$ values in the microgram range. The results are shown in the following Table.

TABLE II

| Group | Wrinkle Index |
| --- | --- |
| Control | 1.6 +/- 0.3 |
| 0.2 μg of Compound A | 0.7 +/- 0.3* |
| 2 μg of Compound A | 0.6 +/- 0.3* |
| 6 μg of Compound A | 0.5 +/- 0.1** |
| 20 μg of Compound A | 0.2 +/- 0.1** |

TABLE II-continued

| Group | Wrinkle Index |
| --- | --- |
| Control | 1.3 +/- 0.2 |
| 0.1 μg of Compound B | 1.3 +/- 0.3 |
| 0.3 μg of Compound B | 0.7 +/- 0.2* |
| 1 μg of Compound B | 0.3 +/- 0.1*** |
| 3 μg of Compound B | 0.2 +/- 0.1*** |

*P < 0.05,
**P < 0.01,
***P < 0.001 vs Control

Creams and gels containing ingredients within the proportions set forth in Examples 3 through 7 below can be formulated by conventional means.

EXAMPLE 3

CREAM

| | % w/w |
| --- | --- |
| Compound A | 0.00001–1.3 |
| Cetyl Alcohol | 1.5 |
| Stearyl Alcohol | 2.5 |
| Span 60 (Sorbitan Stearate) | 2.0 |
| Mineral Oil | 2.0 |
| Arlacel 165 (Glyceryl/PEG 100 Stearate) | 4.0 |
| Tween 60 (Polysorbate 80) | 1.0 |
| Miglyol 818 (Caprylic/Capric/Linoleic triglyceride) | 5.0 |
| Sorbitol Solution | 4.0 |
| Disodium Edetate | 0.1 |
| BHA (Butylated Hydroxyanisole) | 0.05 |
| Methylparaben | 0.18 |
| Propylparaben | 0.05 |
| Water q.s. | 100.00 |

EXAMPLE 4

CREAM

| | % w/w |
| --- | --- |
| A Compound of Formula I | 0.00001–1.0 |
| Cetyl Alcohol | 5.25–8.75 |
| Arlacel 165 (Glyceryl/PEG 100 Stearate) | 3.75–6.25 |
| Miglyol 818 (Caprylic/Capric/Linoleic triglyceride) | 11.25–16.75 |
| Sorbitol Solution | 3.75–6.25 |
| Disodium Edetate | .075–0.125 |
| Carbopol 934P (Carbomer 934P) | 0.15–0.25 |
| BHA (Butylated Hydroxyanisole) | 0.0375–0.0625 |
| Methylparaben | 0.135–0.225 |
| Propylparaben | 0.0375–0.0625 |
| Sodium Hydroxide (10% solution) | 0.15–0.25 |
| Distilled Water, q.s. | 100.00 |

EXAMPLE 5

CREAM

| | % w/w |
| --- | --- |
| A Compound of Formula I | 0.00001–1.0 |
| Cutina MD (Glyceryl Stearate) | 4.5–7.5 |
| Ceteareth-12 | 3.0–5.0 |
| Cetyl Alcohol | 3.0–5.0 |
| Generol 122E-10 (Ethoxylated Soya Sterol) | 2.25–3.75 |

-continued

CREAM

| | % w/w |
|---|---|
| Cetiol LC (Oleic Acid Decyl Ester) | 7.5–12.5 |
| BHA (Butylated Hydroxyanisole) | 0.0375–0.0625 |
| Sorbitol Solution | 3.75–6.25 |
| Disodium Edetate | 0.075–0.125 |
| Methylparaben | 0.135–0.225 |
| Propylparaben | 0.0375–0.0625 |
| Distilled Water, q.s. | 100.00 |

EXAMPLE 6

CREAM

| | w/w |
|---|---|
| Compound B | 0.00001–1.0 |
| Arlatone 983 (PEG 30/Glyceryl Stearate) | 7.0 |
| Cetyl Alcohol | 1.0 |
| Stearic Acid | 4.0 |
| Neobee Oil (Medium chain-length triglyceride) | 17.0 |
| Propylene Glycol | 5.0 |
| 2-phenoxyethanol | 0.5 |
| Distilled Water, q.s | 100.00 |

EXAMPLE 7

GEL

| | % w/w |
|---|---|
| Compound B | 0.00001–1.0 |
| Pluronic L 101 (Polaxamer 331) | 10.00 |
| Aerosil 200 (Silica) | 8.00 |
| PCL Liquid (Fatty Acid Esters) | 15.00 |
| Cetiol V (Decyl Oleate) | 20.00 |
| Neobee Oil (Medium chain-length triglyceride) | 15.00 |
| Euhanol G (Octyldodecanol), q.s. | 100.00 |

Creams of Example 3, wherein Compound A is present in % weight/weight of 0.0001, 0.001. 0.03, 0.01, 0.1 and 0.3 were made and are preferred.

A cream of Example 6 and a gel of Example 7 were made wherein Compound B is present in % weight/weight of 0.5.

It is understood that the proportions of excipients in creams of Examples 3 and 6, and the gels of Example 7 can be varied, if desired, to change the physical properties of the resulting creams and gels.

We claim:

1. A method of treating the conditions associated with photodamaged skin comprising topically administering a compound of the formula

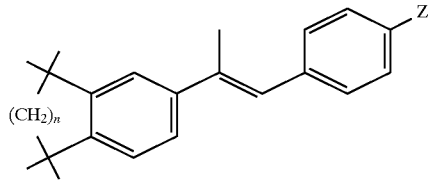

I wherein n represents 1 or 2; Z represents —SO$_2$R, wherein R represents lower-alkyl, lower-alkenyl, lower-alkynyl, lower-alkoxy-lower-alkyl, lower-alkanoyl-lower-alkyl, hydroxy-lower-alkyl, halo-lower-alkyl, lower-carbalkoxy-lower-alkyl, lower-alkoxy, hydroxy, mono-lower-alkyl amino or di-lower-alkylamino, or a pharmaceutically acceptable salt thereof to an area of the skin in need of said treatment, said compound of formula I being applied to said area in an amount effective to reverse the effects of photodamage in said area.

2. A method according to claim 1 wherein R is lower alkyl.

3. A method according to claim 2 wherein the compound of formula I is ethyl p-[2-(5,6,7,8-tetrahydro-5,5,8,8-tetramethyl-2-naphthyl)propenyl]phenylsulfone.

4. A method according to claim 2 wherein the compound of formula I is methyl p-[2-(5,6,7,8-tetrahydro-5,5,8,8-tetramethyl-2-naphthyl)propenyl]phenylsulfone.

5. A method according to claim 2 wherein the compound of formula I is propyl p-[2-(5,6,7,8-tetrahydro-5,5,8,8-tetramethyl-2-naphthyl)propenyl]phenylsulfone.

6. The method of claim 1 wherein the compound of formula I is administered in a topical composition containing at least 0.00001% by weight of said compound of formula I and an inert dermatologically acceptable carrier.

7. The method of claim 6, wherein said topical composition contains a compound of formula I in an amount of from about 0.00001% to about 1.0% by weight of the composition.

8. The method of claim 7, wherein said topical composition contains a compound of formula I n amount of from about 0.0001 to about 0.1% by weight of the composition.

9. The method of claim 8, wherein the compound of formula I is ethyl p-[2-(5,6,7,8-tetrahydro-5,5,8,8-tetramethyl-2-naphthyl)propenyl]phenylsulfone in an amount of about 0.01% to about 0.5% by weight of the composition.

10. The method of claim 7, wherein said composition contains a cosmetically active ingredient.

11. The method of claim 10 wherein said cosmetically active ingredient is a sunscreen.

12. The method of claim 6, wherein said composition is a gel, cream or ointment.

13. The method of claim 6, wherein said composition is applied to the face.

14. A method of treating the conditions associated with photodamage skin comprising topically administering a compound of the formula:

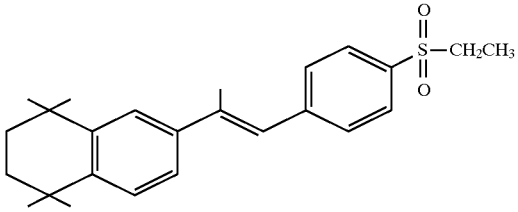

or a pharmaceutically acceptable salt thereof, to an area of the skin in need of said treatment, said compound being applied to said area in an amount effective to reverse the effects of photodamage in said area.

* * * * *